United States Patent
Yotoriyama

(10) Patent No.: US 8,632,998 B2
(45) Date of Patent: Jan. 21, 2014

(54) NUCLEIC ACID ISOTHERMAL AMPLIFICATION METHOD

(75) Inventor: Tasuku Yotoriyama, Tokyo (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 13/214,547

(22) Filed: Aug. 22, 2011

(65) Prior Publication Data

US 2012/0058518 A1 Mar. 8, 2012

(30) Foreign Application Priority Data

Sep. 2, 2010 (JP) .................................. 2010-196609

(51) Int. Cl.
*C12P 19/34* (2006.01)

(52) U.S. Cl.
USPC ...................................................... 435/91.2

(58) Field of Classification Search
USPC ........................................................ 435/91.2
See application file for complete search history.

(56) References Cited

U.S. PATENT DOCUMENTS

2007/0275375 A1* 11/2007 Van Eijk ........................... 435/6
2011/0195457 A1* 8/2011 Nelson et al. ................. 435/91.2

OTHER PUBLICATIONS

Young et al., Nucleic Acids Research, vol. 37, No. 8, e58 pp. 1-8, Mar. 2009.*
Young, et al., "Light-triggered polymerase chain reaction" Chem. Commun., 2008, 462-464.

* cited by examiner

*Primary Examiner* — Cynthia B Wilder
(74) *Attorney, Agent, or Firm* — K&L Gates LLP

(57) ABSTRACT

A nucleic acid isothermal amplification method includes: performing a reverse transcription reaction to reverse-transcribe a target RNA strand into a template DNA strand; irradiating a reaction solution with light to dissociate a photodegradable protecting group bound to a nucleotide in a sequence of an oligonucleotide primer; and performing an amplification reaction for the template DNA strand.

10 Claims, 2 Drawing Sheets

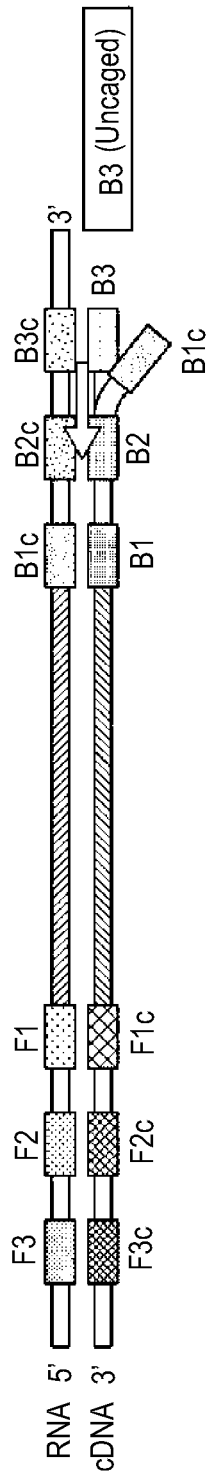
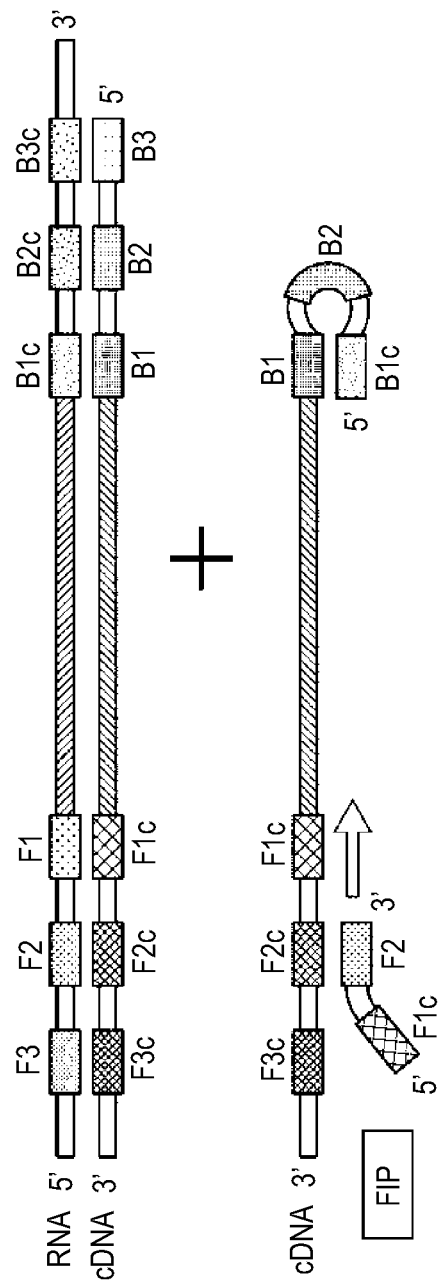
FIG.4A
FIG.4B

NUCLEIC ACID ISOTHERMAL AMPLIFICATION METHOD

CROSS REFERENCES TO RELATED APPLICATIONS

The present application claims priority to Japanese Priority Patent Application JP 2010-196609 filed in the Japan Patent Office on Sep. 2, 2010, the entire content of which is hereby incorporated by reference.

BACKGROUND

The present application relates to nucleic acid isothermal amplification methods, specifically to nucleic acid isothermal amplification methods in which the reverse transcription reaction of the target RNA strand into the template DNA strand is performed in a series of procedures with the amplification reaction of the template DNA strand.

PCR (Polymerase Chain Reaction) has been used as a method of nucleic acid amplification method. In PCR, template DNA strands are amplified by the repeated cycles of three temperature steps including (1) heat denature, (2) annealing, and (3) extension reaction.

In the first heat denature step, the template DNA strands are dissociated into single strands from the double-strands. The reaction temperature for the heat denature is generally about 94° C. In the second annealing step, oligonucleotide primers are bound (annealed) to the single-stranded template DNA strands. The annealing reaction temperature is generally about 50° C. to 60° C. In the third extension reaction, DNA polymerase synthesizes a DNA complementary to the single-stranded portion, using the oligonucleotide primer site as the origin. The reaction temperature for the extension reaction is generally about 72° C.

For gene expression level analyses and cDNA cloning, RT-PCR (Reverse Transcription-Polymerase Chain Reaction) is used in which the reaction of the reverse-transcription of mRNA into cDNA is performed preceding PCR. In RT-PCR, a single-step RT-PCR method has widely been used in which the preceding reverse transcription reaction and the next amplification reaction are performed in a series of procedures.

In the single-step RT-PCR method, a DNA strand (cDNA) complementary to the RNA strand (mRNA) under expression analysis or being cloned is first synthesized by reverse transcription reaction. The reaction is performed with a reaction solution that contains the RNA strand, reverse transcriptase, and reverse-transcription oligonucleotide primers, maintained at a temperature of generally about 42° C. In the next amplification reaction, a PCR reaction is performed using the synthesized DNA strand as a template. The primers used for the amplification reaction are generally selected to bind to the RNA strand (or template DNA strand) base sequence at sites different from the binding sites for the oligonucleotide primers used for the reverse-transcription.

In recent years, an easier method, called isothermal amplification, has come to be used as a nucleic acid amplification method that can obviate the need for the repeated temperature cycles. For example, in LAMP (Loop-Mediated Isothermal Amplification), template nucleic acid strands are mixed with reagents such as oligonucleotide primers, strand displacement-type DNA synthetase, and nucleic acid monomer, and the mixture is held at a constant temperature (in the vicinity of 65° C.) to run the reaction.

In connection with the present disclosure, Light-Triggered Polymerase Chain Reaction, Chem. Commun., 2 008, 462-464 describes a technique for controlling PCR reaction with the use of an oligonucleotide primer that includes a photodegradable protecting group-attached thymine in its base sequence. In this technique, a 6-nitropiperonyloxymethyl (NPOM) group that dissociates by irradiation of UV rays is used as the photodegradable protecting group.

SUMMARY

Techniques that perform the reverse transcription reaction and the amplification reaction in a series of procedures are widely available also in isothermal amplification, as in the case of single-step RT-LAMP. However, unlike PCR, LAMP involves amplification reaction that proceeds at a constant temperature following the reverse transcription reaction. As is known, a drawback of single-step RT-LAMP, then, is the poor reverse transcription reaction efficiency, caused by the amplification reaction that proceeds through strand displacement-type DNA synthetase simultaneously with the reverse transcription reaction promoted by reverse transcriptase. The decreased reverse transcription reaction efficiency lowers the amount of the nucleic acid strand that serves as a template in the amplification reaction, with the result that the accuracy of gene expression level analysis, or the efficiency of cloning may be lowered.

Accordingly, there is a need for a method that can improve the efficiency of the reverse transcription reaction in isothermal amplification in which the reverse transcription reaction and the amplification reaction are performed in a series of procedures.

An embodiment provides a nucleic acid isothermal amplification method that includes: (1) performing a reverse transcription reaction to reverse-transcribe a target RNA strand into a template DNA strand; (2) irradiating a reaction solution with light to dissociate a photodegradable protecting group bound to a nucleotide in a sequence of an oligonucleotide primer; and (3) performing an amplification reaction for the template DNA strand.

In the nucleic acid isothermal amplification method of the embodiment, the oligonucleotide primer includes a photodegradable protecting group-attached nucleotide within its sequence, and thus the binding of the oligonucleotide primer to the complementary strand is inhibited by the photodegradable protecting group in (1). The oligonucleotide primer binds to the complementary strand in (3) only after the photodegradable protecting group has dissociated in (2).

In the nucleic acid isothermal amplification method, it is preferable that the photodegradable protecting group bind to the base portion of the nucleotide, and, for example, a 6-nitropiperonyloxymethyl group is used.

The amplification reaction may be LAMP. In this case, the photodegradable protecting group-attached nucleotide is preferably included in the sequence of the oligonucleotide primer involved in the strand displacement reaction that synthesizes a complementary DNA strand while the target RNA strand is being detached from the template DNA strand.

As used herein, "nucleic acid isothermal amplification reaction" encompasses a variety of nucleic acid amplification reactions that do not involve temperature cycles. The isothermal amplification reaction encompasses a wide range of isothermal reactions intended for nucleic acid amplification, including, for example, LAMP (Loop-Mediated Isothermal Amplification), SMAP (SMart Amplification Process), NASBA (Nucleic Acid Sequence-Based Amplification), ICAN® (Isothermal and Chimeric primer-initiated Amplification of Nucleic acids), TRC (Transcription-Reverse Transcription Concerted) reaction, SDA (Strand Displacement Amplification), TMA (Transcription-Mediated Amplification), and RCA (Rolling Circle Amplification). These nucleic acid amplification reactions include reactions, such as real-time (RT) LAMP, that involve both amplification of nucleic acid strands and quantification of the amplified nucleic acid strands.

The method according to the embodiment can improve the efficiency of the reverse transcription reaction in isothermal amplification in which the reverse transcription reaction and the amplification reaction are performed in a series of procedures.

Additional features and advantages are described herein, and will be apparent from the following Detailed Description and the figures.

BRIEF DESCRIPTION OF THE FIGURES

FIGS. 4A and 4B are diagrams explaining the DNA synthesis reaction at an early stage of amplification reaction.

DETAILED DESCRIPTION

Embodiments of the present application will be described below in detail with reference to the drawings.

1. Nucleic Acid Isothermal Amplification Method According to First Embodiment
   (1) Designing of Oligonucleotide Primers
   (2) Reverse Transcription Reaction
   (3) Degradation of Photodegradable Protecting Group
   (4) Amplification Reaction
2. Variations of Nucleic Acid Isothermal Amplification Method 1. Nucleic Acid Isothermal Amplification Method According to First Embodiment A nucleic acid isothermal amplification method according to First Embodiment includes: (1) performing a reverse transcription reaction to reverse-transcribe a target RNA strand into a template DNA strand; (2) irradiating a reaction solution with light to dissociate a photodegradable protecting group bound to a nucleotide in a sequence of an oligonucleotide primer; and (3) performing an amplification reaction for the template DNA strand.

The following specifically describes the procedure of the nucleic acid isothermal amplification method of First Embodiment with reference to FIG. 1 to FIGS. 4A and 4B, using LAMP-based RT-LAMP as an example of the amplification reaction in (3).

(1) Designing of Oligonucleotide Primers

Figure 1:
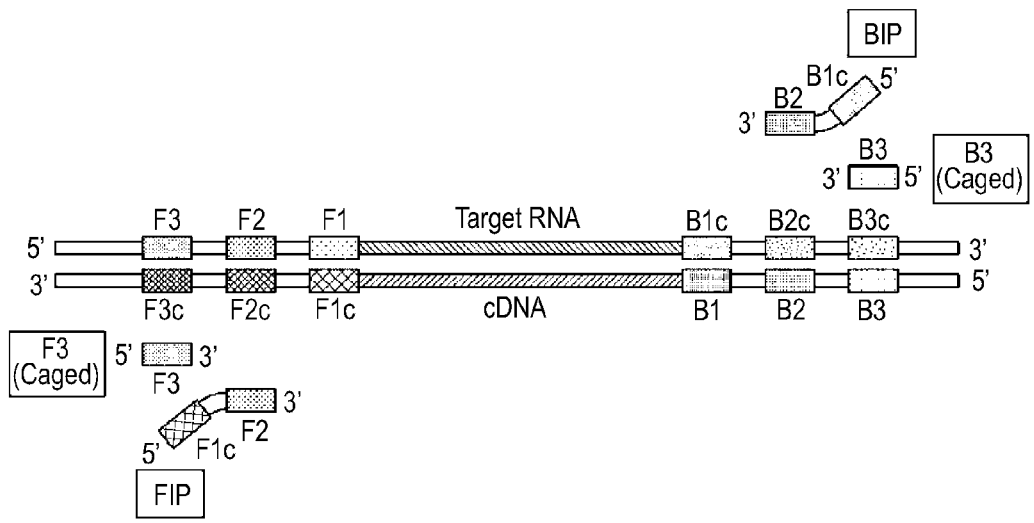
FIG. 1 is a diagram explaining the sequences of a target RNA strand and an oligonucleotide primer.

FIG. 1 is a diagram schematically illustrating the sequences of a target RNA strand (mRNA) and oligonucleotide primers (hereinafter, also referred to simply as "primers"). In RT-LAMP, six regions are selected from the sequence of the target RNA strand, and four kinds of oligonucleotide primers are designed.

The selected regions are F3, F2, F1, and B1c, B2c, B3c from the 5' end of the target RNA strand. The template DNA strand (cDNA) with the base sequence complementary to the target RNA strand has F3c, F2c, F1c, and B1, B2, B3 with the base sequences respectively complementary to the six regions of the target RNA strand.

Primer BIP is designed to have the same base sequences as the regions B1c and B2. Primer B3 has the same base sequence as the region B3. Primer FIP has the same base sequences as the regions F1c and F2. Primer F3 is designed to have the same base sequence as the region F3.

The chain length of each primer is set to have an appropriate melting temperature (Tm) according to the reaction temperatures of the reverse transcription reaction and the amplification reaction. The melting temperatures of the primers are set so that each primer can bind to the target RNA or template DNA under the reaction temperature conditions of the reverse transcription reaction and the amplification reaction. The chain length of the primer is generally about 20 mer.

The sequences of the primers B3 and F3 include a nucleotide bound to a photodegradable protecting group, specifically a 6-nitropiperonyloxymethyl (NPOM) group, as represented in the figure as primer B3 (Caged) and primer F3 (Caged).

Figure 2:
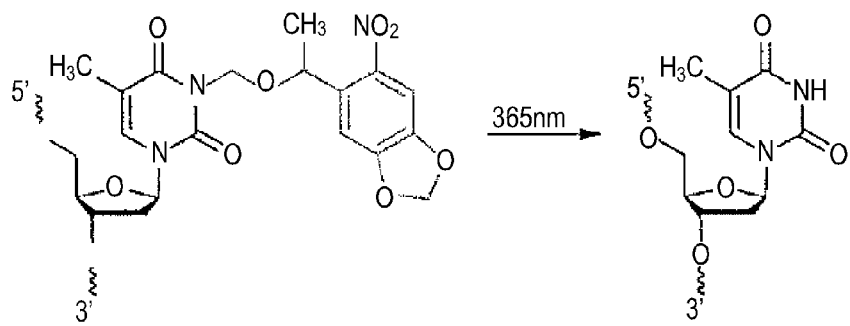
FIG. 2 is a diagram explaining a photodegradation reaction of the 6-nitropiperonyloxymethyl group (NPOM) attached to a nucleotide.

FIG. 2 represents the photodegradation reaction of the NPOM attached to the nucleotide. NPOM is bound to the base (here, thymine (T)) portion of the nucleotide in the primer sequence. The base in the nucleotide forms a hydrogen bond with the complementary base (here, adenine (A)). However, hydrogen bonding does not occur at the nucleotide base bound to NPOM, because the hydrogen atom that contributes to hydrogen bonding is substituted with NPOM. Thus, the primers having an NPOM-attached nucleotide in their sequences have reduced bondability to their complementary strands, and thus lower the melting temperature.

The NPOM attached to the base dissociates by being degraded under UV rays. Dissociating the NPOM frees the base to form a hydrogen bond with its complementary base. Thus, after the NPOM has dissociated from the nucleotide in the primer sequence, the primer recovers its bondability to the complementary strand, and the melting temperature increases.

The number of NPOM-attached nucleotides in the primer sequence is not particularly limited, as long as the melting temperature of the primer is sufficiently different before and after the NPOM dissociation to enable reaction control, as will be described later. The number of NPOM-attached nucleotides may be appropriately selected according to the chain length of the primer. For average chain lengths (about 20 mer), the number of NPOM-attached nucleotides is 1 or 2, or may even be 3 or more.

(2) Reverse Transcription Reaction

Figure 3:
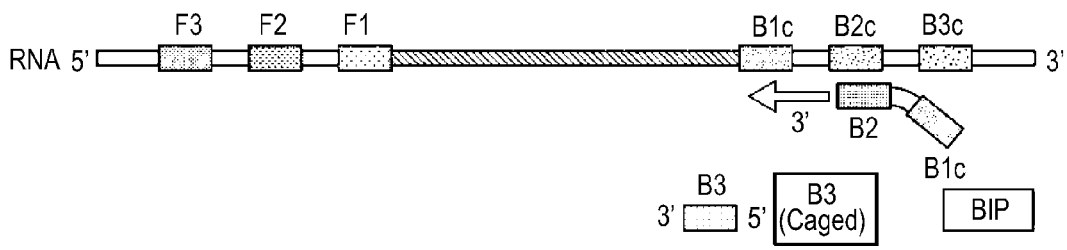
FIG. 3 is a diagram explaining DNA synthesis reaction in a reverse transcription reaction.

FIG. 3 schematically represents DNA synthesis reaction in the reverse transcription reaction.

In the reverse transcription reaction, the target RNA strand and the reaction solution are mixed, and the mixture is maintained at the reaction temperature to synthesize the template DNA strand from the target RNA strand. The reaction solution contains, for example, strand displacement-type DNA synthetase (for example, Bst enzyme), reverse transcriptase (for example, AMV enzyme), primers, nucleic acid monomer (dNTP), and a buffer solute.

In the reverse transcription reaction, the primer BIP binds (anneals) to the region B2c of the target RNA strand, and the template DNA strand complementary to the target RNA strand is synthesized by reverse transcriptase (see the arrow in the figure). Note that, when the target RNA strand shown in the figure is the sense strand accompanied by an antisense RNA strand, the same reverse transcription reaction proceeds from the origin where the primer FIP has bound to the region F2c of the antisense RNA strand.

The reverse transcription reaction is performed at a predetermined reaction temperature (for example, 40° C. to 65°

C.). Any reaction temperature can be chosen, as long as it falls within the temperature range in which the reverse transcriptase is active.

The primer B3 (Caged) and primer F3 (Caged) have low melting temperatures because of the NPOM-attached nucleotides present in their sequences. Thus, the primers B3 and F3 cannot directly bind to the target RNA strand at the reverse transcription reaction temperature or at the amplification reaction temperature (described below).

As such, only the primers BIP and FIP can bind to the target RNA strand in the reverse transcription reaction, and the reverse transcription reaction of the target RNA strand into the template DNA strand efficiently proceeds, using these primers as the origin.

(3) Degradation of Photodegradable Protecting Group

After the reverse transcription reaction, the reaction solution is irradiated with ultraviolet rays to degrade and dissociate the NPOM attached to the nucleotides in the sequences of primers B3 and F3.

Dissociating the NPOM increases the melting temperatures of the primers B3 and F3. This enables the primers B3 and F3 to bind to the target RNA strand at the amplification reaction temperature, as described below.

(4) Amplification Reaction

FIGS. 4A and 4B schematically represent the DNA synthesis reaction at an early stage of the amplification reaction.

In the amplification reaction, the primer B3 after the dissociation of NPOM (primer B3 (Uncaged) in the figure) binds on the outer side of the primer BIP, and a new cDNA is synthesized as the template DNA strand extended from the primer BIP in the reverse transcription reaction is detached from the target RNA strand (see the arrow in FIG. 4A).

When the antisense RNA strand is present, the primer F3 after the dissociation of NPOM binds on the outer side of the primer FIP, and the same strand displacement reaction proceeds. For simplicity, the following only describes the sense strand reaction.

The primer FIP then binds to the region F2c of the template DNA strand extended from the primer BIP and detached from the target RNA strand. Upon the binding of the primer FIP, a DNA strand complementary to the template DNA strand is synthesized by strand displacement-type DNA synthetase, using the primer FIP as the origin (see the arrow in FIG. 4B).

Primer F3 then binds on the outer side of the primer FIP, and a new DNA strand is synthesized as the DNA strand complementary to the template DNA strand and extended by the strand displacement-type DNA synthetase from the primer FIP is detached (not illustrated). The detached DNA strand complementary to the template DNA strand is then used as the origin structure of the amplification cycle to run the amplification reaction for the template DNA strand in the same manner as in the common LAMP.

The amplification reaction is performed at a predetermined reaction temperature (for example, 40° C. to 65° C.). Any reaction temperature may be chosen, as long as it falls within the temperature range in which the strand displacement-type DNA synthetase is active.

In the nucleic acid isothermal amplification method according to First Embodiment, NPOM is attached to the nucleotide in the sequence of primer B3 (and primer F3) to control and prevent the binding of the primer B3 (Caged) to the target RNA strand in the reverse transcription (see FIG. 3). Further, by dissociating the NPOM attached to the nucleotide in the sequence of primer B3 in the degradation of the photodegradable protecting group, the primer B3 (Uncaged) can be controlled to bind to the target RNA strand only in the amplification reaction (see FIG. 4A).

Binding of the primer B3 to the target RNA strand in the reverse transcription reaction causes the template DNA strand extended from the primer BIP to be detached by the cDNA extended from the primer B3 that has bound on the outer side of the primer BIP. Further, the primer B3 non-specifically attached to the target RNA strand may inhibit the synthesis of the template DNA strand from the primer BIP. In either case, the efficiency of the reverse transcription reaction may be lowered.

The nucleic acid isothermal amplification method according to First Embodiment controls the binding and dissociation of NPOM to enable the primer B3 to bind to the target RNA strand only in the amplification reaction. It is therefore possible to prevent the efficiency of the reverse transcription reaction from being lowered by the binding of the primer B3 to the target RNA strand in the reverse transcription reaction.

2. Variations of Nucleic Acid Isothermal Amplification Method

In the foregoing First Embodiment, the nucleic acid isothermal amplification method was described through the case of the NPOM-attached nucleotide being present only in the sequence of primer B3 (and primer F3). However, the NPOM-attached nucleotide also may be present in the primer BIP (and primer FIP). It is, however, required that primer B3 include greater numbers of NPOM-attached nucleotides than primer BIP. Specifically, the primer B3 needs to have a lower melting temperature than the primer BIP by including greater numbers of NPOM-attached nucleotides. In this case, the primer B3 can be controlled not to bind to the target RNA strand by making the reaction temperature of the reverse transcription reaction higher than the melting temperature of the primer B3. Further, by making the reaction temperature of the amplification reaction lower than the melting temperature of the primer B3 freed from the NPOM, the primer B3 can be controlled to bind to the target RNA strand in the amplification reaction following the degradation of the photodegradable protecting group.

Further, in the foregoing First Embodiment, the nucleic acid isothermal amplification method was described through the use of NPOM as the photodegradable protecting group. However, the photodegradable protecting group is not particularly limited, provided that it can bind to the base portion of the nucleotides in the primer sequence to inhibit the formation of a hydrogen bond between the base and the complementary base, and that it can be degraded by irradiation of light to cancel the inhibitory action. The base attached to the photodegradable protecting group is not limited to thymine (T), and may be adenine (A), cytosine (C), or guanine (G), depending on the protecting group used.

A photoresponsive substance that undergoes conformational (cis-trans) changes in response to light may be used in place of the photodegradable protecting group. Such a photoresponsive substance may be, for example, azobenzene, which has use in the photoregulation of nucleic acid double strand formation as reported in Photoregulation of DNA Triplex Formation by Azobenzene, J Am Chem Soc. 2002, Vol. 124, No. 9, p. 1877-83. The hydrogen bond between base pairs can be made stable or unstable in a reversible fashion by binding azobenzene to the base portion of the nucleotides or to the strand structural portion of the nucleotides (pentose and ester bond), and by converting the conformation by irradiation of light. The primer attached to azobenzene can thus have different melting temperatures before and after the conformational change, and the reaction can be controlled in the same manner as with the case of the primer attached to the photodegradable protecting group.

The nucleic acid isothermal amplification method according to First Embodiment can improve the efficiency of the reverse transcription reaction, and can thus improve the accuracy and efficiency of gene expression level analyses and cloning.

It should be understood that various changes and modifications to the presently preferred embodiments described herein will be apparent to those skilled in the art. Such changes and modifications can be made without departing from the spirit and scope and without diminishing its intended advantages. It is therefore intended that such changes and modifications be covered by the appended claims.

The application is claimed as follows:

1. A nucleic acid isothermal amplification method, comprising:
    performing a reverse transcription reaction to reverse-transcribe a target RNA strand into a template DNA strand, comprising mixing the target RNA strand with a reaction solution to form a mixture, the reaction solution containing a photodegradable protecting group bound to a nucleotide in a sequence of an oligonucleotide primer;
    irradiating the mixture with light to dissociate the photodegradable protecting group; and
    performing an isothermal amplification reaction for the template DNA strand.

2. The method according to claim 1, wherein the photodegradable protecting group is bound to a base portion of the nucleotide.

3. The method according to claim 2, wherein the photodegradable protecting group is a 6-nitropiperonyloxymethyl group.

4. The method according to claim 3, wherein the isothermal amplification reaction is Loop-Mediated Isothermal Amplification (LAMP).

5. The method according to claim 4, wherein the isothermal amplification reaction includes a strand displacement reaction that synthesizes a complementary DNA strand while the template DNA strand is being detached from the target RNA strand, and wherein the oligonucleotide primer is involved in the strand displacement reaction.

6. The method according to claim 2, wherein the base portion is thymine.

7. The method according to claim 1, wherein the oligonucleotide primer is a Loop-Mediated Isothermal Amplification (LAMP) primer selected from the group consisting of: FIP, BIP, F3 and B3.

8. The method according to claim 1, wherein the isothermal amplification reaction is selected from the group consisting of: SMart Amplification Process (SMAP), Nucleic Acid Sequence-Based Amplification (NASBA), Isothermal and Chimeric primer-initiated Amplification of Nucleic acids (ICAN), Transcription-Reverse Transcription Concerted reaction (TRC), Strand Displacement Amplification (SDA), Transcription-Mediated Amplification (TMA) and Rolling Circle Amplification (RCA).

9. The method according to claim 1, wherein the isothermal amplification reaction is performed after the mixture has been irradiated with light.

10. The method according to claim 1, wherein the reaction solution comprises reverse transcriptase.

* * * * *